(12) United States Patent
Popescu et al.

(10) Patent No.: US 7,940,399 B2
(45) Date of Patent: May 10, 2011

(54) JONES PHASE MICROSCOPY OF TRANSPARENT SAMPLES

(75) Inventors: Gabriel Popescu, Champaign, IL (US); Zhuo Wang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 143 days.

(21) Appl. No.: 12/460,808

(22) Filed: Jul. 24, 2009

(65) Prior Publication Data

US 2010/0027027 A1   Feb. 4, 2010

Related U.S. Application Data

(60) Provisional application No. 61/086,012, filed on Aug. 4, 2008.

(51) Int. Cl.
*G01B 11/02* (2006.01)
(52) U.S. Cl. ............................................. 356/495
(58) Field of Classification Search ............... 356/491, 356/495
See application file for complete search history.

(56) References Cited

U.S. PATENT DOCUMENTS

| | | | |
|---|---|---|---|
| 6,342,945 B1 * | 1/2002 | Allen et al. ............... | 356/73.1 |
| 6,441,902 B1 * | 8/2002 | Hilfiker et al. ............ | 356/369 |
| 6,801,312 B1 * | 10/2004 | Tiwald ..................... | 356/369 |
| 6,898,537 B1 * | 5/2005 | McGahan ................. | 702/76 |
| 7,115,858 B1 * | 10/2006 | Holden et al. ............. | 250/225 |
| 7,372,565 B1 * | 5/2008 | Holden et al. ............. | 356/327 |
| 2002/0085195 A1 * | 7/2002 | Allen et al. .............. | 356/73.1 |

OTHER PUBLICATIONS

De Boer, et al., "Review of polarization sensitive optical coherence tomography and Stokes vector determination" Jul. 2002, Journal of Biomecial Optics, vol. 7., No. 3. pp. 359-371.*
de Boer et al., "Review of polarization sensitive optical coherence tomography and Stokes vector determination," *Journal of Biomedical Optics*, 7(3), pp. 359-371, Jul. 2002.
Popescu, "Quantitative phase imaging and applications: a review," http://light.ece.uiuc.edu/QPI_review.htm, pp. 1-32, (Oct. 5, 2006).

* cited by examiner

*Primary Examiner* — Patrick J Connolly
(74) *Attorney, Agent, or Firm* — Sunstein Kann Murphy & Timbers LLP

(57) ABSTRACT

Methods for displaying anisotropic properties of an object. The object is illuminated with a first test beam characterized by a first polarization that, after traversing the object, is combined with a reference beam. The combined light of the first transmitted test beam and the reference beam is analyzed by a first pair of polarization analyzers, and interference created between the first transmitted test beam and the reference beam as analyzed by the first pair of analyzers is detected to derive intensity, phase and polarization of the first transmitted test beam. The same is then done with a second test beam that has a polarization with a component orthogonal to the first polarization. Based on the two analyzed beams, complex elements of a Jones matrix associated with the object in a local coordinate system are determined and a plurality of tangible images are displayed that characterize the object based on the complex elements of the Jones matrix.

11 Claims, 4 Drawing Sheets

(A)

(B)

(C)

(D)

JONES PHASE MICROSCOPY OF TRANSPARENT SAMPLES

The present application claims the priority of U.S. Provisional Application 61/086,012, filed Aug. 4, 2008, which is incorporated herein by reference.

FIELD OF INVENTION

The present invention relates to a method for polarization-sensitive imaging, revealing information about anisotropic properties of a transparent sample.

BACKGROUND ART

Phase imaging techniques, which allow for quantifying optical phase delays experienced by light interacting with matter, have received increasing interest over the past decade, particularly in the context of biological imaging used to define morphology and dynamics of live cells. Various single-point and full-field techniques have been developed, including optical coherence tomography (OCT) and phase-contrast OCT (PC-OCT, used to quantify phase retardation in biological samples), Fourier phase microscopy (FPM, utilizing the scattered and unscattered light from the object as the object and reference fields in an interferometer), Hilbert phase microscopy (HPM, allowing to obtain phase images from only one spatial interferogram recording), and diffraction phase microscopy (that combines the single-shot feature of HPM with the common-path geometry of FPM). See, e.g., G. Popescu, "Quantitative phase imaging and application: a review" (2006, available at http://light.ece.uiuc.edu/QPI_review.htm). Polarization-sensitive versions have been demonstrated for some of the foregoing techniques.

Polarization-sensitive phase imaging techniques generally allow for detection of changes in the polarization state of light as it interacts with the sample. Such techniques may improve imaging contrast. In prior art, polarization information has been processed and presented by utilizing the well-known Stokes vector and Mueller matrix. The Stokes-Mueller formalism is based on the intensity of polarized light transmitted through a sample as a function of the polarization state of the incident light. It has been assumed that an intensity-based approach provides all the information necessary for analyzing a material, and thus the Stokes-Mueller formalism naturally lends itself as an algorithm for analyzing the images. See, e.g., M. Mujat, "*Polarimetric characterization of random electromagnetic beams and applications*," University of Central Florida, 2004, for a review.

SUMMARY OF THE INVENTION

In accordance with embodiments of the present invention, a method is provided for for displaying anisotropic properties of a physical object. The method has steps of:

a. illuminating the physical object with a first test beam characterized by a first polarization;

b. combining with a reference beam a first transmitted test beam that has traversed the physical object;

c. analyzing combined light of the first transmitted test beam and the reference beam by means of a first pair of polarization analyzers;

d. detecting interference created between the first transmitted test beam and the reference beam as analyzed by the first pair of analyzers to derive intensity, phase and polarization of the first transmitted test beam, e. illuminating the physical object with a second test beam characterized by a second polarization, the second polarization having a component orthogonal to the first polarization;

f. analyzing combined light of the second transmitted test beam and the reference beam by means of a second pair of polarization analyzers;

g. detecting interference created between the second transmitted test beam and the reference beam as analyzed by the second pair of analyzers to derive intensity, phase and polarization of the second transmitted test beam;

h. determining complex elements of a Jones matrix associated with the physical object in a local coordinate system based on the intensity, phase and polarization of the first and second transmitted test beams; and i. displaying a plurality of particular visual depictions characterizing the physical object based on the complex elements of the Jones matrix.

In accordance with alternate embodiments of the invention, the step of analyzing combined light of the first transmitted test beam and the reference beam may be performed by applying the first pair of polarization analyzers in temporal succession, and the first pair of polarization analyzers may also include a single polarization analyzer successively applied in distinct polarizations.

Similarly, the step of analyzing combined light of the second transmitted test beam and the reference beam may performed by applying the second pair of polarization analyzers in temporal succession, and the second pair of polarization analyzers includes a single polarization analyzer successively applied in distinct polarizations.

In accordance with further embodiments of the invention, at least one particular visual depiction of the plurality of particular visual depictions may represent a modulus of an element of the Jones matrix for each pixel of the particular visual depiction, and at least one particular visual depiction of the plurality of particular visual depiction represents a phase of an element of the Jones matrix for each pixel of the particular visual depiction. There may also be an additional step of acquiring, with the set of optical detectors, at least one reference interferogram, formed by the test and the reference beams traversing only the isotropic space.

In accordance with another aspect of the invention, a particular visual depiction of a physical object is provided, where the physical object has a polarizing characteristic. The particular visual depiction is formed by:

a. illuminating the physical object with a first test beam characterized by a first polarization;

b. combining with a reference beam a first transmitted test beam that has traversed the physical object;

c. analyzing combined light of the first transmitted test beam and the reference beam by means of a first pair of polarization analyzers;

d. detecting interference created between the first transmitted test beam and the reference beam as analyzed by the first pair of analyzers to derive intensity, phase and polarization of the first transmitted test beam, e. illuminating the object with a second test beam characterized by a second polarization, the second polarization having a component orthogonal to the first polarization;

f. analyzing combined light of the second transmitted test beam and the reference beam by means of a second pair of polarization analyzers;

g. detecting interference created between the second transmitted test beam and the reference beam as analyzed by the second pair of analyzers to derive intensity, phase and polarization of the second transmitted test beam;

h. determining complex elements of a Jones matrix associated with the physical object in a local coordinate system based on the intensity, phase and polarization of the first and second transmitted test beams; and i. creating a particular visual depiction characterized by an array of values corresponding to the complex elements of the Jones matrix associated with the physical object.

In other embodiments of the invention, the array of values may represent a modulus of an element of the Jones matrix, and the array of values may also represent an argument of an element of the Jones matrix.

BRIEF DESCRIPTION OF THE DRAWINGS

Advantages of the present invention and its several improvements will be seen when the following detailed description is read in conjunction with the attached drawings. These drawings are intended to provide a better understanding of the present invention, but they are in no way intended to limit the scope of the invention.

DESCRIPTION OF SPECIFIC EMBODIMENTS OF THE INVENTION

Definition of Terms

Figure 1:
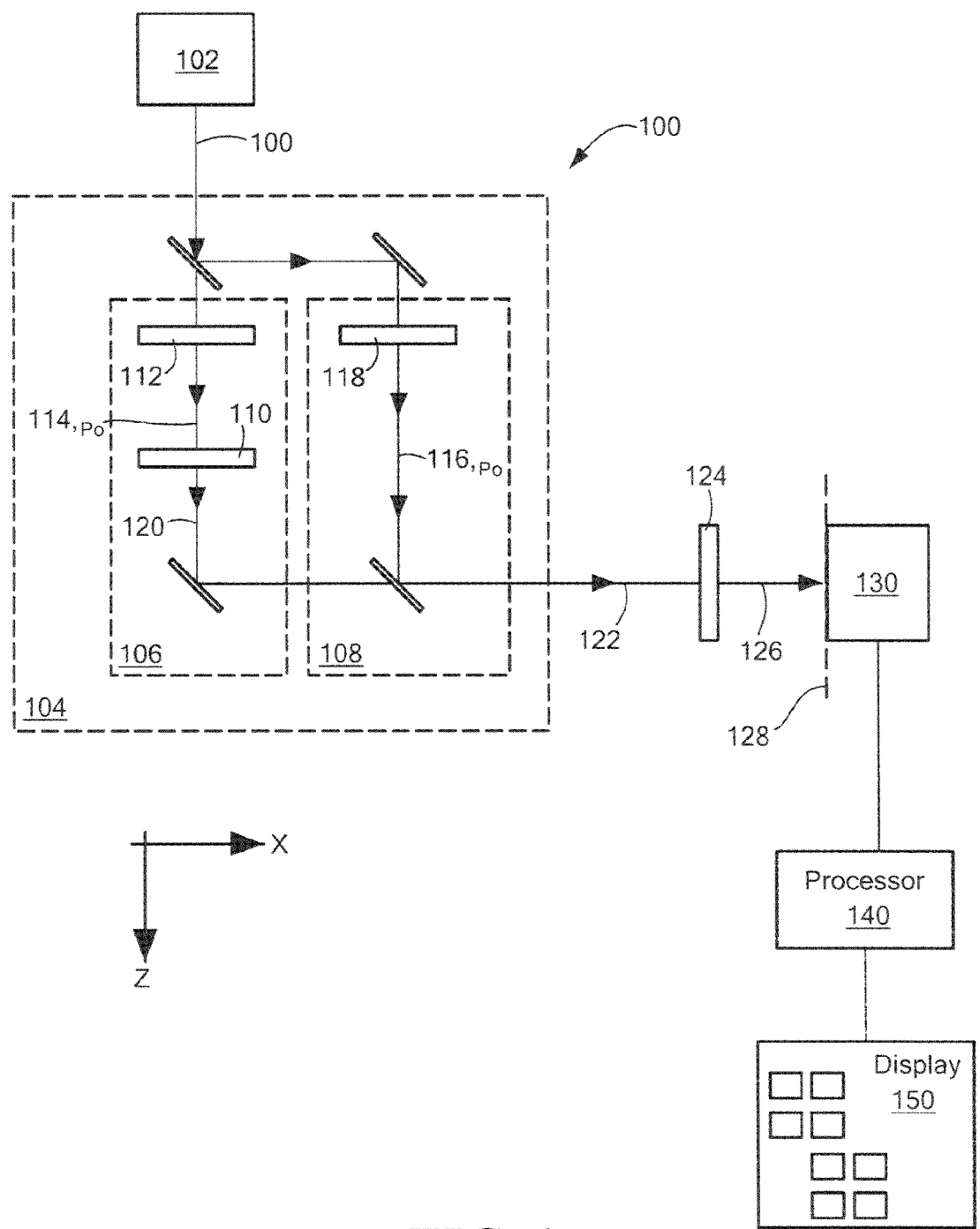
FIG. 1 is a schematic depiction of an interferometric system, in accordance with an embodiment of the present invention, as used in measuring and displaying, the anisotropic properties of an object.

Unless the context otherwise requires, in the description of the invention and accompanying claims the following terms will have meanings as defined below:

A "set" denotes either a unit or a collection of more than one unit.

A "physical object," for purposes of the present description and any appended claims, is an object that exists at a particular time and place and that is characterized both by mass and spatial extent.

An "image" refers to an ordered representation of scalar values corresponding to spatial positions. For example, an image may be an array of values within an electronic memory or storage medium, or, alternatively, a visual image may be formed on a display device such as a video screen or printer. A "visual depiction" of an object may be sensed by human vision in such a way that characteristic features of the object may be recognized.

"Orthogonal polarizations" of light are polarizations described by electric field vectors the inner product of which is substantially zero.

A "transfer function" associated with an imaged object is understood as a mathematical representation, in terms of spatial distribution, of a relation between characteristics of light prior to traversal of the object and the same characteristics of the light subsequent to traversal of the object.

Interaction of an optical field with an object that transmits light (such as biological tissue, for example) is largely determined by the three-dimensional distribution of the refractive index associated with the object, and may be represented, equivalently, as modifications of the wavefront of an illuminating field upon traversing the object. By quantifying the optical path length shift associated with such object, one can non-invasively probe anisotropic properties of the object. Embodiments of the present invention image anisotropic properties of a transparent object by extracting polarization transfer properties of the object from interferograms based on light transmitted through the object. In a specific embodiment, the polarizing properties of the object may be presented in the form of a polarization transfer matrix such as the Jones matrix associated with the object represented in a local frame of reference.

Polarization-based techniques such as those of the present invention can reveal inner structure of cells without requiring exogenous contrast agents. The present invention additionally quantifies optical phase delays through the sample, which, in the context of live cells, may also advantageously provide intrinsic information about cell morphology and dynamics.

Although embodiments of the invention are described in the context of imaging using a microscope objective and are referred to as Jones phase microscopy, it will be understood that any other optical imaging system such as a telescope, for example, may be used in interferometric configuration to provide interferograms containing information about the polarization transfer function of the imaged object.

The representation of a polarization transfer function in terms of a 2×2 "field-based" matrix formalism was first described by R. C. Jones, "New calculus for the treatment of optical systems," *J. Opt. Soc. Am.*, 31, pp. 488-493, (1941), which is incorporated herein by reference. However, its application in full-field imaging has not been practical, and, so, has not been considered. De Boer and Milner, (*J. of Biomed. Opt.*, v. 7, pp. 359-371, July 2002) taught away from the use of the Jones matrix formalism in polarization-sensitive imaging techniques because their measurement was intensity-based.

It does not come as a surprise, therefore, that a Jones matrix representation of the optical phase delays or field rotations experienced by light traversing a sample has not been exploited in the prior art, whether in the characterization of biological samples such as live cells or otherwise.

One embodiment of an interferometric system used in measuring and, then, displaying, the anisotropic properties of an object is now described with reference to FIG. 1. FIG. 1 schematically depicts an embodiment of a system, designated generally by numeral 100, which may be used for practicing methods of the current invention. The configuration may use a modified version of a Hilbert phase microscope described in Ikeda et al., *Opt. Lett.*, v. 30, pp. 1165-1168 (2005), which is incorporated herein by reference. Substantially monochromatic light 101 from a light source 102, such as a He—Ne laser, for example, is coupled into an interferometer 104 having a test arm 106 (or "object arm") and a reference arm 108. While a Mach-Zehnder interferometric configuration is depicted, it is to be understood that the present invention is not so limited.

A transparent object 110, disposed in test arm 106, is illuminated with a test beam 114 of light from the test arm 106, suitably collimated, and having a pre-determined polarization, defined by a polarizer 112. Polarizer 112 may be compound, particular in that it may be called upon to transform any elliptical polarization of light 101 into a linear polarization along controllable directions. A reference beam of light 116, passing through the reference arm 108 of the interferometer 104, has a polarization set by a polarizer 118. At any instant, polarizations of the beams 114 and 116 overlap to some degree, which is to say the scalar product ("dot" product) of their vector directions is not zero. In preferred embodiments of the invention, in fact, their polarizations are substantially the same (denoted as $P_O$ in FIG. 1) where the polarization $P_O$ is chosen from a set of polarizations that span the space of polarizations, as described below.

A set of orthogonal polarizations, for purposes of the present invention, is a pair of polarizations that, taken together, span the vector space of polarization vectors and that, additionally, have no projection on one another, i.e., their scalar product is null. Well-known examples of orthogonal polarizations are the linear polarizations that are perpendicular to each other and fixed in time, and right and left circular polarizations where the polarization direction in space varies with the phase of the wave.

At a position further down the optical train, the sample is imaged, by means of an inverted microscope, or otherwise, and the image is related to a detector array 130 via a lens system with a specified magnification. The reference beam 116, suitably collimated, and the beam 120, formed upon test beam 114 exiting the object 110, substantially overlap in space to form a light beam 122, then pass through an analyzer 124 and interfere, as a light output 126, in a plane 128.

In order to facilitate the optimal use of various optical elements of the embodiment 100 such as polarizers or spectral filters which may be optionally added by the user, the light beams traversing such elements may be collimated. However, differently shaped beams may be used as may be appropriate for a particular application. In some embodiments, a small spatial angle between the substantially overlapped collimated test and reference beams 120 and 116 may be preserved in forming the light output beam 126 so as to generate a number of interference fringes, in the CCD plane 128, to be substantial enough for a detailed reconstruction of the data obtained from the sampled interferograms.

Interferograms formed in the plane 128 by the light output 126 are acquired with the use of an optical detector array 130 comprising, for example, a charge-coupled device (CCD) detector array. Output from the detector array 130 is further directed to a processor 140 configured to analyze the acquired interferograms and to retrieve information about the polarizing properties of the object 110. Images derived by processor 140 as described herein are then displayed by means of display device 150.

A polarization state $P_A$ of the light output 126 may be set by the analyzer 124 based on the polarization $P_O$ of the beams 114 and 116 so as to enable a determination of the polarization transfer function of the object 110 from the acquired interferograms, as discussed below.

Figure 2:
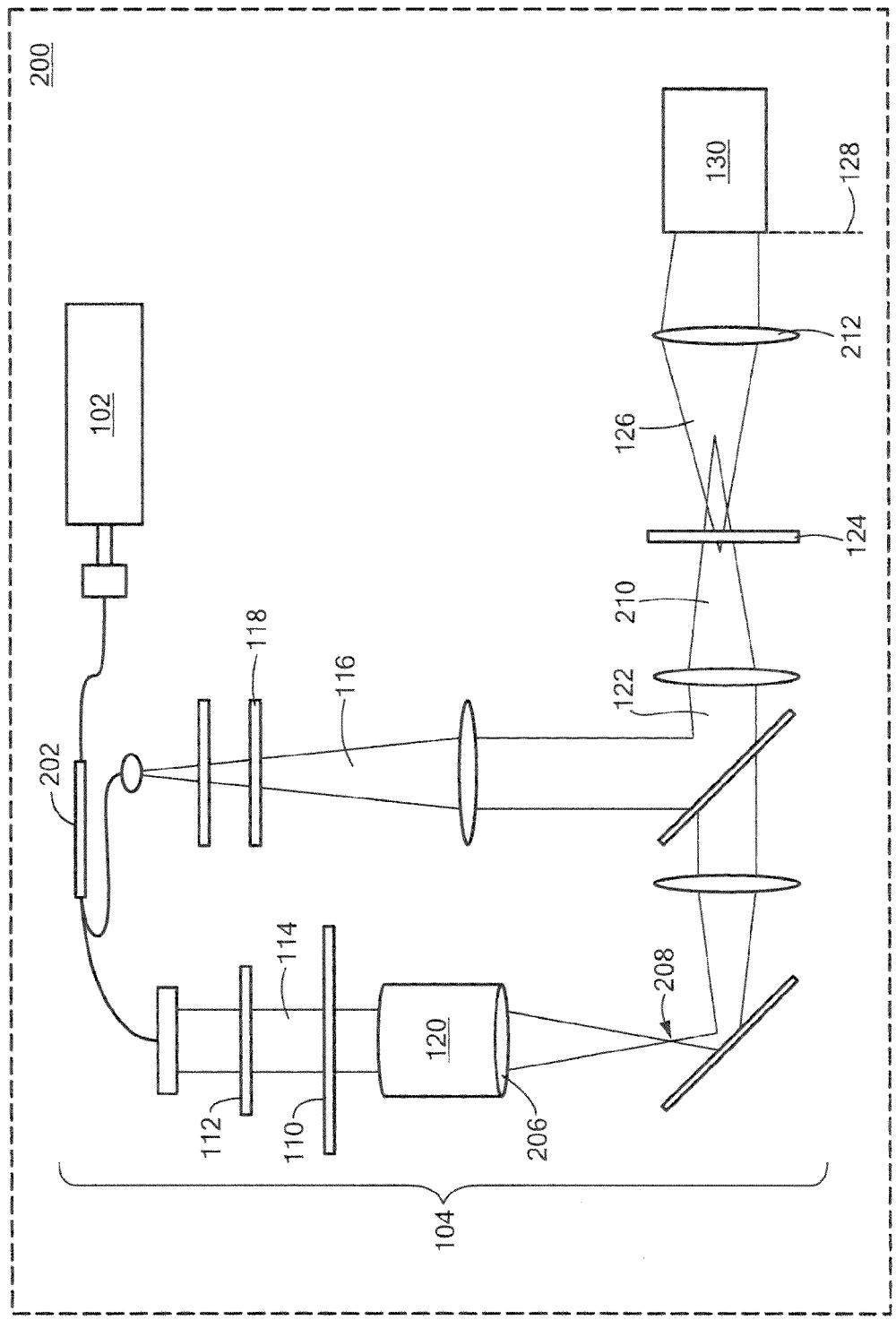
FIG. 2 is a schematic depiction of an interferometric system for deriving a Jones matrix representation of transmission through an object, in accordance with a further embodiment of the present invention.

In an alternate embodiment 200 depicted in FIG. 2 a fiber-optic splitter 202 divides the incident monochromatic beam between a test beam and a reference beam. A full-field image of the object 110, formed by a lens 206 at a focal point 208, is further relayed by a beam 210 via a lens 212 to the CCD 130. As shown, the embodiment 200 employs a modified version of a Hilbert phase microscope described, for example, by Popescu et al., *Erythrocyte structure and dynamics quantified by Hilbert phase microscopy*, J. Biomed. Opt. Lett., v. 10, p. 060503, (2005), which is incorporated herein by reference in its entirety. However, any other suitable imaging system such as a telescope, for example, may be used for relaying either of the beams 114 or 116 down the optical train.

With reference to FIGS. 3(a)-(d), the determination of the polarization transfer matrix of the object 110 according to an embodiment of the method of the invention may be carried out based on measurements of several interferograms formed with different combinations of polarizers 112 and 118 and analyzer 124, as shown successively in FIGS. 3(a)-(d). In one embodiment, such determination may be accomplished by analyzing four interferograms as follows.

The first two interferograms (FIGS. 3(a) and 3(b)) are formed with nominal polarizations of the beams 114 and 116 chosen to be a first polarization $P_{O1}$, while the second two interferograms (FIGS. 3(c) and 3(d)) are formed using a second polarization $P_{O2}$, such that polarizations $P_{O1}$ and $P_{O2}$ together span the space of polarizations. Polarizations $P_{O1}$ and $P_{O2}$ may be orthogonal, as shown in FIGS. 3(a) and 3(b), however, within the scope of the invention, they need not be orthogonal, as long as they together span the space of polarizations Consider two orthogonal unit vectors, $$\begin{bmatrix} 1 \\ 0 \end{bmatrix}, \text{ and } \begin{bmatrix} 0 \\ 1 \end{bmatrix},$$

that span the space of polarizations, For two linear electric vectors, $P_{O1}$ and $P_{O2}$, respectively oriented at +45° and −45° to reference axis $$\begin{bmatrix} 1 \\ 0 \end{bmatrix},$$

for example, the successive input polarizations may be expressed in the form of Jones vectors, as $$P_{O1} = C_1 \begin{bmatrix} 1 \\ 1 \end{bmatrix} \text{ and } P_{O2} = C_2 \begin{bmatrix} 1 \\ -1 \end{bmatrix}, \qquad \text{(Eq. 1)}$$

where $C_1$ and $C_2$ are, most generally, complex constants, although, in the embodiment considered here, they are real constants. The first two interferograms may be formed with polarizations of the beams 114 and 116 being substantially the same as $P_{O1}$, as defined by the polarizers 112 and 118, respectively. The nature and orientation of the analyzer 124 in a particular embodiment depends on the nature and orientation of the polarizers 112 and 118. In this embodiment, one interferogram is formed with the linear analyzer 124 initially having its transmission axis parallel to the reference axis, while another interferogram is formed with the transmission axis of the analyzer 124 being perpendicular to the reference axis. Similarly, to form the third and the forth interferograms the polarizers 112 and 118 are appropriately rotated to match polarizations of the beams 114 and 116 with the remaining polarization, $P_{O2}$, from the set of orthogonal polarizations, and the analyzer 124 is oriented in parallel and perpendicular to the reference axis, as described above. In a related alternative embodiment, orientations of the polarizers 112 and 118 may be chosen in reverse order as compared to the embodiment described above.

Figure 3:
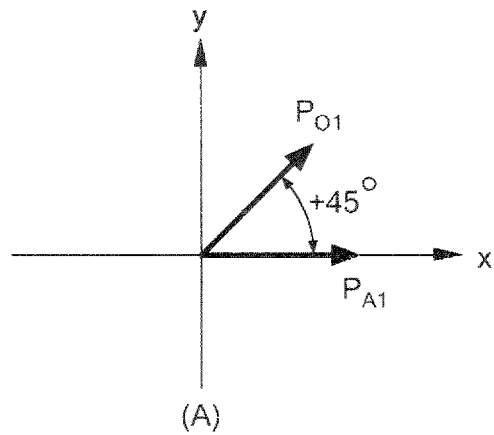
FIG. 3(a-d) represent one constellation of four relative orientations of incident polarization and analyzer for deriving the complex Jones matrix terms in accordance with one embodiment of the present invention.
Figure 3:
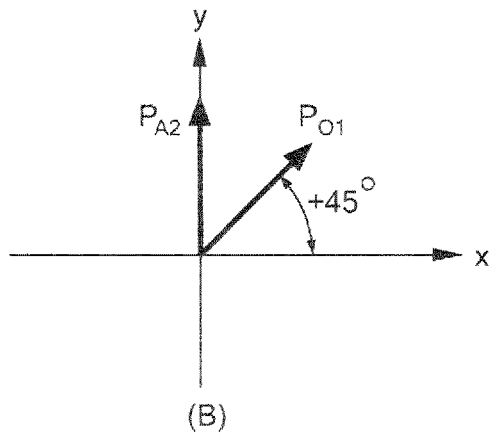
Figure 3:
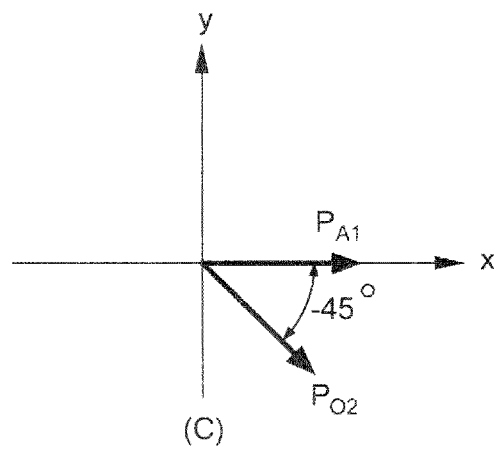
Figure 3:
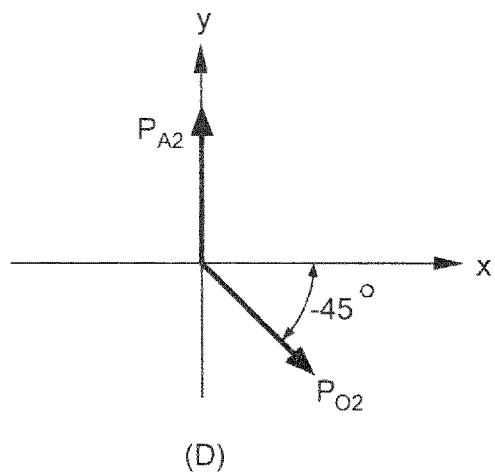
Figure 4:
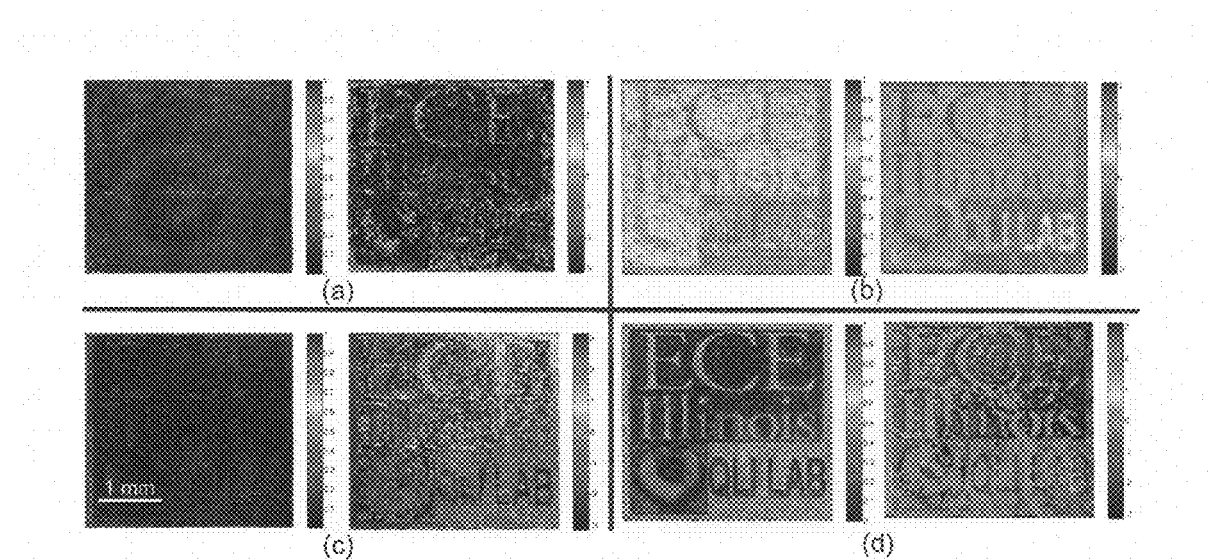
FIGS. 4(a-d) show tangible images of an object (in this case, a spatial light modulator made of twisted nematic liquid crystal) with the modulus and phase, in respective left-right pairs, of the four elements of a Jones matrix representation, in accordance with an embodiment of the present invention.
Figure 5:
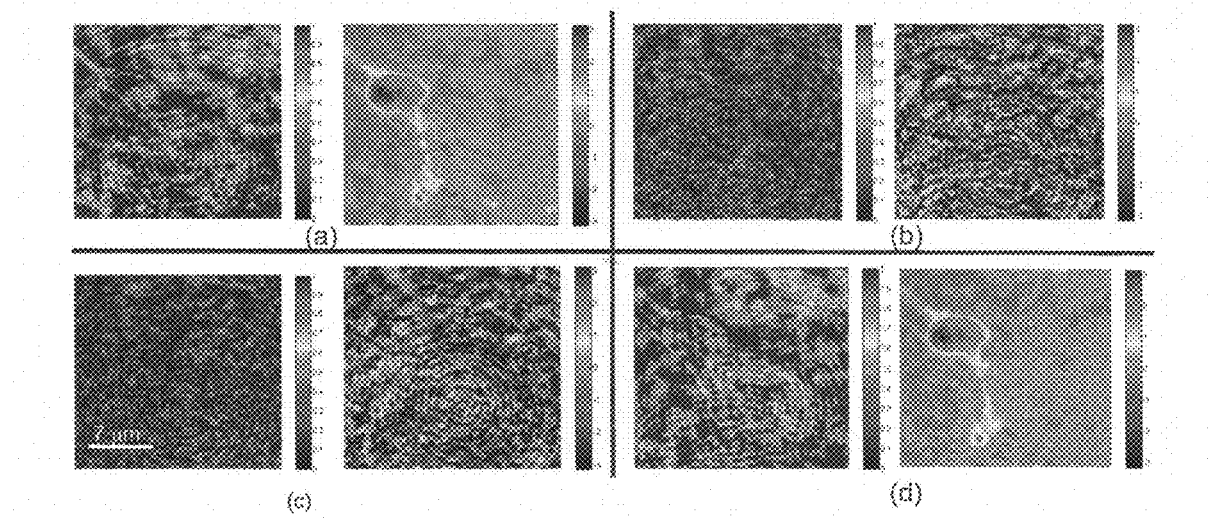
FIGS. 5(a-d) show tangible images of a live neuron, with the modulus and phase, in respective left-right pairs, of the four elements of a Jones matrix representation, in accordance with an embodiment of the present invention.

The combinations of orientations of all the polarizing elements employed in the abovementioned specific embodiment to form the four interferograms that contain sufficient information to describe the polarization transferring properties of the object 110 are illustrated in FIG. 3, with the x-axis arbitrarily chosen to represent the reference axis. It shall be appreciated that from the four resulting interferograms $Y_{ij}$ (where i,j=1,2), respectively corresponding to the orientation of polarizing elements as shown in FIGS. 3(a) through 3(d), both the phase and the amplitude images can be derived that aggregately provide sufficient information to fully determined the polarization transfer function of the object 110. The quantitative phase images associated with the object may be reconstructed using a two-dimensional spatial Hilbert transform, as described, for example, by Ikeda et al. in *Opt. Lett.*, 30, 1165-1168 (2005), which is incorporated herein by reference, or any other suitable method known in the art.

Expressing the polarization transfer function, associated with the object in the local coordinate system, in terms of a Jones matrix, $$J \equiv \begin{bmatrix} J_{11} J_{12} \\ J_{21} J_{22} \end{bmatrix},$$

the complex interferometric images $Y_{ij}$ can be re-written in a matrix form as Y=C·J or, more particularly, as $$\begin{bmatrix} Y_{11} \\ Y_{21} \\ Y_{12} \\ Y_{22} \end{bmatrix} = \begin{bmatrix} C_1 & C_1 & 0 & 0 \\ C_2 & -C_2 & 0 & 0 \\ 0 & 0 & C_1 & C_1 \\ 0 & 0 & C_2 & -C_2 \end{bmatrix} \begin{bmatrix} J_{xx} \\ J_{xy} \\ J_{yx} \\ J_{yy} \end{bmatrix}. \quad \text{(Eq. 2)}$$

To analyze the images $Y_{ij}$ optimally, the constants $C_1$ and $C_2$ may be determined by performing an additional measurement of a reference interferogram formed, in a fashion similar to that described with reference to FIG. 3, with no sample in the tests arm of an employed embodiment of the interferometer. (The Jones matrix corresponding to such object-absentee is known to be the two-by-two identity matrix.) Following the determination of the constants $C_i$, the four complex elements of the matrix J may be further determined based on registered images $Y_{ij}$ by inversion of Eq. 2.

The determined complex elements of the polarization transfer matrix of the object 110 may be further mapped across a field of view that adequately characterizes the spatial extent of the object. Such spatial distribution of the polarization transferring properties of the object may be presented to the user, for example, in a form of one or more extracted images representing the modulus of, or phase of, a particular element of the polarization transfer matrix, or both.

To resolve the ambiguity inherent in experimental determination of the phase components of the matrix elements, in a related embodiment of the invention, additional interferograms are obtained with no sample present (or, alternatively, in transmission through an isotropic portion of the sample disposed in the test arm). This provides a common phase reference for the respective elements of the Jones matrix.

By way of a non-limiting example illustrating an embodiment of the invention, FIGS. 4(a)-(d) demonstrate a set of four phase maps and a set of four respectively corresponding modulus maps, of the elements of the Jones matrix of an object, obtained from the interferograms registered according to the above-described embodiment of the method. In this example, the object 110 was configured to include a controllable spatial light modulator (SLM) made of a twisted nematic liquid crystal with a vertical linear polarizer placed in front of the SLM and aligned with its principal axis so that the expected Jones matrix representing such object would contain non-zero terms only in the right column.

FIGS. 4(a)-(d) each corresponds to a tangible image of the complex Jones matrix element representative of a physical object as obtained with the polarizing elements described with reference to FIGS. 3(a) through 3(d). In each of the image-subsets, the image on the left represents a modulus map of a corresponding matrix element, while the image on the right represents a respective phase map (i.e., an argument of the complex matrix element). The individual images of the elements of the Jones matrix shown in FIGS. 4(a) and 4(b) characterize the polarizing properties of the object. In particular, as seen in FIG. 4, the modulus images of FIGS. 4(a) and 4(c) corresponding to the elements $J_{11}$ and $J_{21}$ (left column of the Jones matrix of the object) demonstrate a substantially zero amplitude, to within the noise level. The corresponding phase maps are rather noisy, as expected, because these phase maps are associated with optical fields of very low amplitudes, for which phases are not well defined. Both the phase and amplitude images of FIGS. 4(b) and 4(d), corresponding to the elements $J_{21}$ and $J_{22}$, on the other hand, are reconstructed with high signal-to-noise ratio and show the image pattern defined by the SLM. In each of FIGS. 4(a)-4(d), and in FIGS. 5(a)-5(d) described below, the left image is an amplitude map and the right image is a phase map, with the color bar denoting arbitrary units in the case of amplitude, an phase in radians, in the case of the phase maps.

A further non-limiting example illustrating an embodiment of the invention is depicted in FIGS. 5(a)-(d), each of which shows an amplitude modulus map and a corresponding phase map, of one element of the Jones matrix of a live neuron. These are obtained from the interferograms registered according to the above-described embodiment of the method.

The embodiments of the invention described above are intended to be merely exemplary; numerous variations and modifications will be apparent to those skilled in the art. For example, although the embodiments of the invention have been discussed with reference to a particular, linear-vector set of orthogonal polarizations (of light beams propagating through the test and reference arms of the interferometric set-up of the invention), it shall be understood that a choice of different polarizers defining a different set of orthogonal polarizations and an appropriate choice of a different analyzer does not change the principle of operation of the embodiments of the invention. In addition, interferograms may be formed and registered sequentially or in parallel, depending on a particular implementation of the interferometric setup. All such variations and modifications are intended to be within the scope of the present invention as defined in any appended claims. Further description of the invention is provided in Wang et al., *Jones Phase Microscopy of Transparent and Anisotropic Samples, Optics Lett.*, vol. 33, pp. 1270-72 (2008), which is incorporated herein in its entirety.

What is claimed is:

1. A method for displaying anisotropic properties of a physical object, the method comprising:
    a. illuminating the physical object with a first test beam characterized by a first polarization;
    b. combining with a reference beam a first transmitted test beam that has traversed the physical object;
    c. analyzing combined light of the first transmitted test beam and the reference beam by means of a first pair of polarization analyzers;

d. detecting interference created between the first transmitted test beam and the reference beam as analyzed by the first pair of analyzers to derive intensity, phase and polarization of the first transmitted test beam, e. illuminating the object with a second test beam characterized by a second polarization, the second polarization having a component orthogonal to the first polarization;

f. analyzing combined light of the second transmitted test beam and the reference beam by means of a second pair of polarization analyzers;

g. detecting interference created between the second transmitted test beam and the reference beam as analyzed by the second pair of analyzers to derive intensity, phase and polarization of the second transmitted test beam;

h. determining complex elements of a Jones matrix associated with the physical object in a local coordinate system based on the intensity, phase and polarization of the first and second transmitted test beams; and i. displaying a plurality of particular visual depictions of the physical object based on the complex elements of the Jones matrix.

2. A method according to claim 1, wherein the step of analyzing combined light of the first transmitted test beam and the reference beam is performed by applying the first pair of polarization analyzers in temporal succession.

3. A method according to claim 1, wherein the first pair of polarization analyzers includes a single polarization analyzer successively applied in distinct polarizations.

4. A method according to claim 1, wherein the step of analyzing combined light of the second transmitted test beam and the reference beam is performed by applying the second pair of polarization analyzers in temporal succession.

5. A method according to claim 1, wherein the second pair of polarization analyzers includes a single polarization analyzer successively applied in distinct polarizations.

6. A method according to claim 1, wherein at least particular visual depiction of the plurality of particular visual depictions represents a modulus of an element of the Jones matrix for each pixel of the particular visual depiction.

7. A method according to claim 1, wherein at least one particular visual depiction of the plurality of particular visual depictions represents a phase of an element of the Jones matrix for each pixel of the particular visual depiction.

8. A method according to claim 1, further comprising:
acquiring, with the set of optical detectors, at least one reference interferogram, formed by the test and the reference beams traversing only the isotropic space.

9. A particular visual depiction of a physical object having a polarizing characteristic, the particular visual depiction formed by:

a. illuminating the physical object with a first test beam characterized by a first polarization;

b. combining with a reference beam a first transmitted test beam that has traversed the physical object;

c. analyzing combined light of the first transmitted test beam and the reference beam by means of a first pair of polarization analyzers;

d. detecting interference created between the first transmitted test beam and the reference beam as analyzed by the first pair of analyzers to derive intensity, phase and polarization of the first transmitted test beam, e. illuminating the physical object with a second test beam characterized by a second polarization, the second polarization having a component orthogonal to the first polarization;

f. analyzing combined light of the second transmitted test beam and the reference beam by means of a second pair of polarization analyzers;

g. detecting interference created between the second transmitted test beam and the reference beam as analyzed by the second pair of analyzers to derive intensity, phase and polarization of the second transmitted test beam;

h. determining complex elements of a Jones matrix associated with the object in a local coordinate system based on the intensity, phase and polarization of the first and second transmitted test beams; and i. creating a particular visual depiction characterized by an array of values corresponding to the complex elements of the Jones matrix associated with the physical object.

10. A particular visual depiction according to claim 9, wherein the array of values represent a modulus of an element of the Jones matrix.

11. A particular visual depiction according to claim 9, wherein the array of values represent an argument of an element of the Jones matrix.

* * * * *